United States Patent
Doorenbos et al.

[11] 3,931,325
[45] Jan. 6, 1976

[54] PERFLUOROCYCLOHEXENE-1,4-DIONE

[75] Inventors: Harold E. Doorenbos, Midland; Hughie R. Frick, Bay County, both of Mich.

[73] Assignee: The Dow Chemical Company, Midland, Mich.

[22] Filed: Mar. 4, 1974

[21] Appl. No.: 448,135

[52] U.S. Cl.... 260/586 R; 260/63 UY; 260/63 HA; 260/617 R
[51] Int. Cl.² ........................................ C07C 49/48
[58] Field of Search ............................. 260/586 R

[56] References Cited
UNITED STATES PATENTS

| | | | |
|---|---|---|---|
| 3,306,936 | 2/1967 | Anello et al. | 260/586 R |
| 3,379,765 | 4/1968 | Anello et al. | 260/586 R |

OTHER PUBLICATIONS

Ogden, et al., "J. Chem. Soc.," (C) 1971, pp. 2920-2926, (C.A. 95:118293Z).
Jida et al., "Chem. Abstracts," 66:8650m (1967).

*Primary Examiner*—Norman Morgenstern
*Attorney, Agent, or Firm*—Glenn H. Korfhage

[57] ABSTRACT

Two new organic compounds are disclosed, perfluorocyclohexane-1,4-dione and perfluorocyclohexene-1,4-dione, which are obtained concurrently or alternatively by reacting fluoranil with substantially pure anhydrous cobalt trifluoride. These compounds are clear, colorless liquids which are useful as monomers in the synthesis of thermally stable elastomeric polymers. Also disclosed is the dihydrate of said perfluorocyclohexane-1,4-dione, namely, octafluoro-1,1,4,4-cyclohexanetetraol. Another aspect of this invention is a series of polyethers formed by reacting said perfluorocyclohexane-1,4-dione with cesium fluoride and a cyclic or noncyclic aliphatic perhaloalkene having from 2 to 12 carbon atoms and a fluorine atom on at least each of the carbon atoms connected by the double bond, said polymer having as a repeating unit

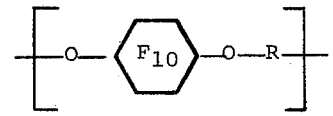

wherein
R is a divalent radical selected from the group consisting of

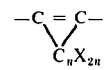 and 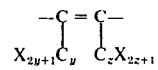

wherein
X is a halogen selected from the group consisting of fluorine, chlorine, bromine, iodine, or any stable combination thereof within the same molecule;
$n$ is an integer of from 1 to 4;
$y$ is an integer of from 0 to 10; and
$z$ is an integer of from 0 to (10-$y$).

When of sufficiently high molecular weight or when lightly cross-linked, these polymers are elastomers having high thermal stability.

2 Claims, 4 Drawing Figures

PERFLUOROCYCLOHEXENE-1,4-DIONE

NOTICE OF GOVERNMENTAL INTEREST

The invention herein described was made in the course of or under a contract or subcontract thereunder, with the Department of the Navy.

BACKGROUND OF THE INVENTION

Rausch et al. in *J. Org. Chem.* 28, 494 (1963) teach use of cobalt trifluoride to achieve the addition of fluorine to double bonds in noncyclic aliphatic compounds. However, few examples of perfluorinated diketones are reported, and prior to the invention disclosed herein, it is believed that no cyclic perfluorinated ketones were known in which the ketone functions were not vicinal.

SUMMARY OF THE INVENTION

Each of perfluorocyclohexane-1,4-dione,

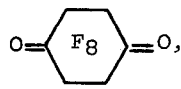

and perfluorocyclohexene-1,4-dione,

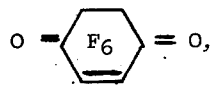

are recovered from the reaction product of 2,3,5,6-tetrafluoro-benzoquinone, commonly known as fluoranil, with substantially pure anhydrous cobalt trifluoride. These new compounds are both clear, colorless liquids useful as intermediates in the preparation of polymers which are in the nature of mixed perfluorinated polyethers.

In a further aspect of this invention, perfluorocyclohexane-1,4-dione is treated with cesium fluoride in a nonpolar, water miscible aprotic solvent medium to which is added a perhaloalkene having from 2 to 12 carbon atoms and a fluorine atom on at least each of the carbon atoms connected by the double bond. When the reaction is substantially complete, conventional techniques are employed to recover various components from the reaction mixture, including a polymer having as a repeating unit

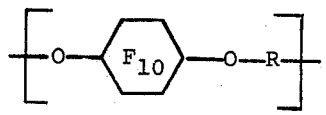

wherein R is a divalent radical selected from the group consisting of

 and 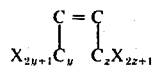

wherein X is halogen selected from the group consisting of fluorine, chlorine, bromine, iodine, or any stable combination thereof within the same molecule;
$n$ is an integer of from 1 to 4;
$y$ is an integer of from 0 to 10; and
$z$ is an integer of from 0 to (10-y).

These clear, colorless oils can be subjected to cross-linking in a manner conventional to fluoroolefins to form elastomers having outstanding chemical and thermal stability useful as sealants, gaskets, flexible coatings, and the like.

Finally, by treating at least the solid phase of the polymer reaction medium with water after the reaction is substantially complete and following said water treatment step with an extraction step, octafluoro-1,1,4,4,-cyclohexanetetraol is recovered. This white solid has a melting point of 175°–176° C. and has utility as a flame retardant and as an intermediate to the formation of perfluorocyclohexane-1,4-dione on dehydration.

FURTHER DESCRIPTION OF THE INVENTION

Figure 1:
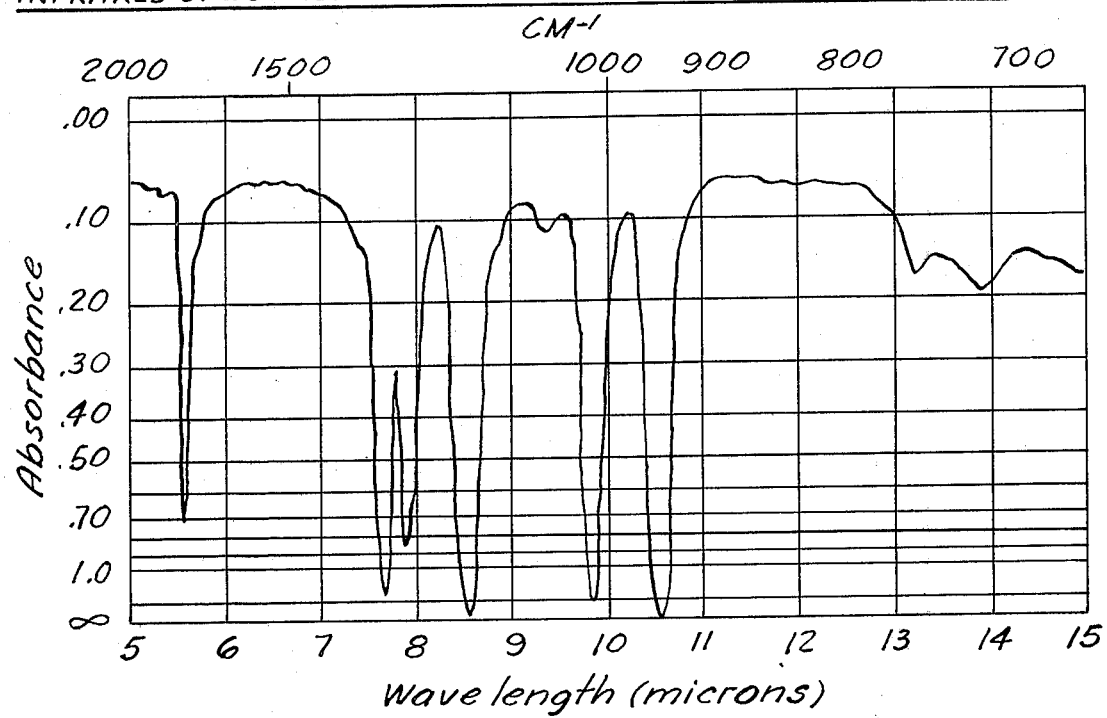
FIG. 1 is a reproduction of a spectrophotometer recording showing the absorption of light in the infrared region of the spectrum by the compound prepared as described in Examples I–VI and identified as perfluorocyclohexane-1,4-dione.

A. Preparation of Perfluorocyclohexane-1,4-dione and Perfluorocyclohexene-1,4-dione:

Each of the above-named compounds was prepared from (1) fluoranil, which had been freshly recrystallized from carbon tetrachloride to assure high purity, and (2) substantially pure anhydrous cobalt trifluoride. The purity of the starting materials, particularly the cobalt trifluoride, is critical in order to avoid contamination of the desired cyclic end products with ring scission products. It has been found advantageous to further dry even so-called pure cobalt trifluoride available commercially and to agitate the freshly dried product in the presence of chlorine trifluoride at about 305° C. to about 310° C. prior to reaction with the fluoranil.

In theory, four moles of cobalt trifluoride are required to react with one mole of fluoranil to form one mole of perfluorocyclohexane-1,4-dione. To obtain maximum yield of the completely fluorinated compound, however, it is preferred to react the CoF₃ and the fluoranil in a mole ratio of from about 6:1 to about 20:1. Appreciable recovery of both the saturated and mono-unsaturated ring compounds is realized, i.e., each compound is recoverable in greater than what might be considered "trace" yields, where a starting molar ratio of from about 8:1 to about 20:1 is employed. Where a molar ratio of cobalt trifluoride to fluoranil of about 5:1 to about 8:1 is employed, recovery of the mono-unsaturated ring compound is to be expected over the saturated compound.

In practicing this invention, a quantity of freshly dried cobalt trifluoride is placed in a suitable reaction vessel while maintaining therein an inert atmosphere such as nitrogen. While continuing to maintain the inert atmosphere, a preselected quantity of fluoranil and a solubilizing amount of a halocarbon solvent are added to the reaction vessel and the vessel is then closed.

Exemplary of the halocarbon solvent suitable for use herein are $CFCl_3$, $CF_2Cl_2$, $CF_3Cl$, $CCl_2FCClF_2$ and the like; thus, fluorocarbon products currently sold under the Freon brand name are acceptable, as are many other commercially available products such as the 3M Company's FC-75 brand cyclic perfluorinated ether. Generally, however, the more highly fluorinated compounds are preferably for use herein, since it has been found that when $CFCl_3$ is employed as a solvent, for example, one of the chlorine atoms tends to be replaced by a fluorine atom, and the displaced chlorine atom in turn reacts with the perfluorocyclohexene-1,4-dione to form a small amount of

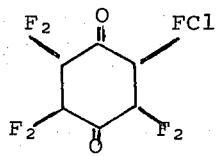

The contents of the charged reaction vessel are agitated while at a temperature of from about 70° C. to about 130° C. for from about 6 hours at the higher temperatures to up to about 96 hours at the lower temperatures. While this temperature range is operable, in most instances it is preferred to operate at from about 95° C. to about 115° C., since the higher the reaction temperature, the greater the risk of degradation of the basic molecular structure. Temperatures below about 95° C. prolong the reaction time. Within the preferred temperature range, the reaction equilibrium is usually substantially reached after from about 12 to about 36 hours and often after from about 18 to about 24 hours.

When the reaction is substantially complete, the reaction medium is cooled to room temperature, i.e., about 20° C., and evacuated, i.e., vaporized at pressures on the order of about 1 $\mu$ Hg through a series of cold traps to separate the various components of the medium. While no effort has been made to determine with precision the temperatures at which the desired products may be recovered at such a pressure, as a generalization, perfluorocyclohexene-1,4-dione, can be collected in a trap maintained at about −20° C., and perfluorocyclohexane-1,4-dione is recoverable in a trap maintained at about −50° C. It has been found convenient to use two-stage trap separation processes, such as those hereinafter more fully described in Examples I and II. Those skilled in the art are readily capable of choosing a cold trap separation process which will suit their needs based on the teachings herein.

The examples which follow further illustrate the present invention and the manner in which it can be practiced; these examples and those set forth later in the specification should be construed merely as being representative and not as limitations on the overall scope of the invention.

EXAMPLE I

Under a nitrogen atmosphere, a 90 milliliter volume corrosion resistant metal cylinder was charged in the order named with approximately 27.6 grams (0.238 mole) of freshly regenerated anhydrous cobalt trifluoride, approximately 3.6 grams (0.02 mole) of fluoranil recrystallized from carbon tetrachloride, and approximately 20 milliliters of Freon 12 brand difluorodichloromethane. The cylinder was closed and placed in a furnace maintained at about 97°-98° C. wherein it was rotated for approximately 22 hours. Upon cooling to room temperature, the reaction mixture of the cylinder was evacuated through a series of three cold traps under a pressure of on the order of 1 $\mu$ Hg. In the first trap, maintained at about −78° C., perfluorocyclohexane-1,4-dione and a small amount of an unidentified acid fluoride were collected. Small amounts of the same materials were collected in a second trap which was also maintained at about −78° C. In the third trap, maintained at about −196° C., traces of each of chlorine, carbonyl fluoride ($COF_2$), and trifluorochloromethane were found along with most of the difluorodichloromethane used as a solvent. The contents of the two −78° C. traps, totalling 3.5 grams, were passed through a second series of traps maintained at −50° C., −78° C., and −196° C. The −50° C. trap collected 2.1 grams of a clear, colorless liquid which subsequently was determined by mass, NMR, and infrared spectroscopy to be perfluorocyclohexane-1,4-dione; the −78° C. trap collected 1.1 grams of a mixture of the diketone and the unidentified acid fluoride; and the −196° C. trap contained a material consisting solely of about 0.3 grams of the unidentified acid fluoride.

EXAMPLE II

Following substantially the same initial procedures as described in Example I, 11.0 grams (0.0949 mole) of regenerated anhydrous cobalt trifluoride, 3.2 grams (0.0178 mole) of recrystallized fluoranil, and 10 ml. of Freon 11 brand of fluorotrichloromethane were maintained with agitation at about 110°-111° C. for about 18 hours. Under vacuum, the cooled reaction medium was passed through a series of cold traps maintained at −45° C., −78° C., and −196° C., respectively. The contents of the first two traps were thereafter passed through a second series of traps maintained at −20° C., and at −78° C., from which were recovered 1.8 grams and 1.3 grams, respectively, of clear, colorless liquid. After further purification by passage through a ¼ inch × 20 foot ethylenepropylene wax gas chromatographic column, each of the two liquids was subsequently analyzed using mass, NMR, and infrared spectroscopy. The liquid recovered in the −20° C. trap was identified as perfluorohexene-1,4-dione, and that recovered in the −78° C. trap was identified as perfluorohexane-1,4-dione.

EXAMPLES III – VI

In basically similar procedures using slightly different quantities of starting materials, reaction temperatures, and reaction times, the results tabulated in Table I were obtained.

TABLE I

| Ex. No. | Quantity Fluoranil Grams(moles) | Quantity CoF₃ Grams(moles) | Solvent | Temp. °C. | Time Hours | O=⟨F₈⟩=O Grams | O=⟨F₆⟩=O Grams | Acid Fluoride | COF₂ | Recovered Fluoranil |
|---|---|---|---|---|---|---|---|---|---|---|
| III | 0.8 (.0044) | 11.3 (0.096) | CF₃Cl | 75 | 72 | — | 0.15 | — | — | * |
| IV | 2.0 (0.0111) | 9.3 (0.0802) | Freon 113 | 95 | 96 | * | 0.6 | — | — | 1.3 |
| V | 2.9 (0.0161) | 16.2 (0.14) | CFCl₃ | 110 | 66 | 2.3 | — | 0.7 | * | * |
| VI | 2.5 (0.0139) | 14.8 (0.127) | CFCl₃ | 111 | 21 | 1.8 | — | ~1.3 | * | — |

\* Trace or somewhat larger quantities.

Figure 2:
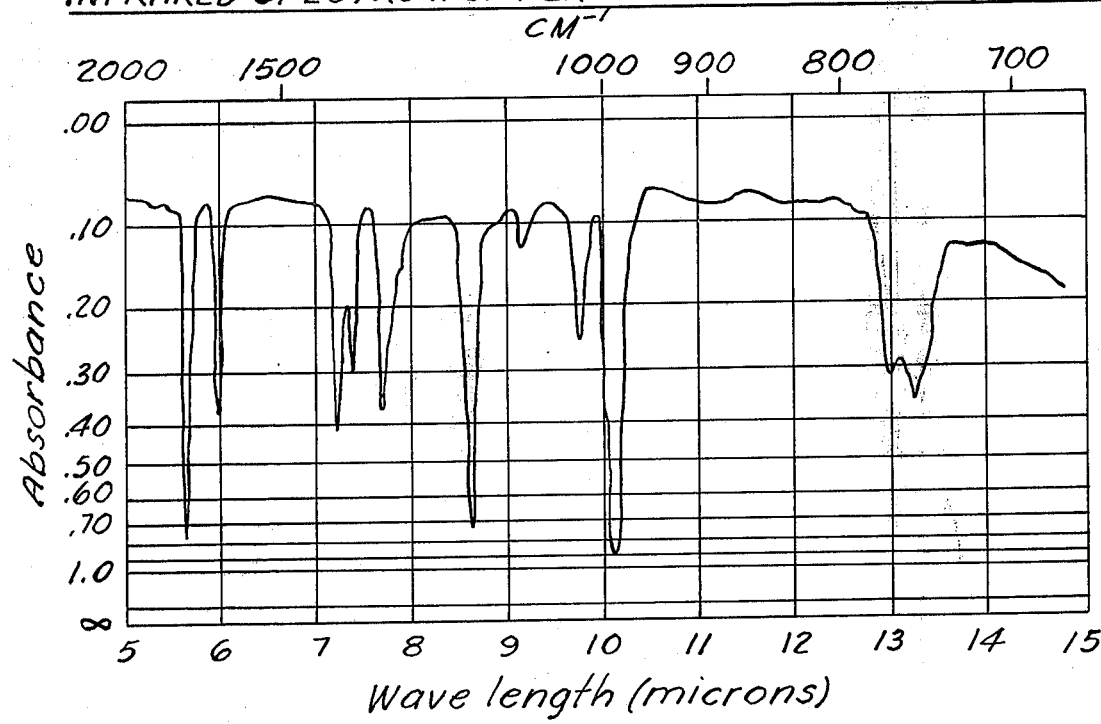
FIG. 2 is a similarly reproduced recording showing the absorption of light in the infrared region of the spectrum by the compound prepared as described in Examples I–VI and identified as perfluorocyclohexene-1,4-dione.

Boiling points at atmospheric pressure have been estimated from vapor pressure measurements to be about 110° C. for perfluorohexane-1,4-dione and about 140° C. for perfluorohexene-1,4-dione. Infrared spectra for these two compounds are shown in FIG. 1 and FIG. 2, respectively. Perfluorocyclohexane-1,4-dione having a formula weight of 256.053 grams per mole exhibited mass spectral peaks as follows:

| m/e | Fragment |
|---|---|
| 256 | Molecular ion (M⁺) |
| 109 | (CF—CF₂—CO)⁺ |
| 100 | (CF₂CF₂)⁺ |
| 31 | (CF)⁺ |

Similarly, the following mass spectral peaks were observed for perfluorocyclohexene-1,4-dione, which has a formula weight of 218.056 grams per mole:

| m/e | Fragment |
|---|---|
| 218 | Molecular ion (M⁺) |
| 168 | (CF₂COCF=CF—CO)⁺ |
| 109 | (CF—CF₂—CO)⁺ |

The nuclear or fluorine magnetic resonance (NMR) spectrum of fluorine for each compound was recorded at 56.4 megacycles in the customary manner using fluorotrichloromethane as an internal standard. Principal characteristic absorption peaks occurred at the following frequencies, expressed in δ units: perfluorocyclohexane-1,4-dione, 125.5; perfluorocyclohexene-1,4-dione, 131.0 and 126.1.

B. Preparation of Polymers from Perfluorocyclohexane-1,4-dione

To prepare copolymers having as a repeating unit

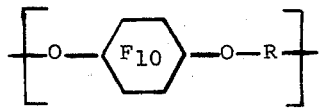

wherein R is a divalent radical selected from the group consisting of

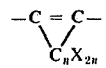 and 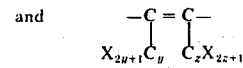

wherein X is halogen selected from the group consisting of fluorine, chlorine, bromine, iodine, or a stable combination thereof within the same molecule;

$n$ is an integer of from 1 to 4;

$y$ is an integer of from 0 to 10; and $z$ is an integer of from 0 to (10-y), the following procedure is generally followed:

Under a dry inert atmosphere, e.g., nitrogen, a preselected amount of anhydrous cesium fluoride, which serves as polymerization reaction promoter, is placed in a suitable reaction vessel, preferably one constructed from glass. To this is added a solubilizing amount of an anhydrous, water miscible, nonpolar, aprotic solvent, for example, dioxane or tetrahydrofuran, or, more preferred, a polyglycol ether such as any of diethylene glycol dimethyl ether, diethylene glycol diethyl ether, or triethylene glycol dimethyl ether and the like. As an indication of what is meant by "solubilizing amount" in this context, in the uusual practice of this invention, from about 2 milliliters to about 10 milliliters, and preferably from about 2.5 milliliters to about 4 milliliters, of solvent is employed per gram of cesium fluoride. Sufficient perfluorocyclohexane-1,4-dione is added to the reaction vessel under a partial vacuum to provide a diketone:cesium fluoride molar ratio of about 1:2, although the ratio may be increased slightly to obtain shorter reaction times, or, decreased to obtain higher polymers in longer reaction times.

The diketone, cesium fluoride, and solvent are agitated at ambient temperature until a uniform, finely dispersed slurry is formed, usually within from about 2 to about 12 hours, although it is not detrimental to agitate the mixture for longer periods if more convenient, e.g., overnight. The slurry is cooled with, for example, liquid nitrogen, and under a vacuum a perhaloalkene is added, said alkene having from 2 to 12 carbon atoms and a fluorine atom on at least each of the two carbon atoms connected by the double bond. The perhalo-substituted alkene may be either cyclic or noncyclic. When a cyclic alkene is selected, R in the above formula will correspond to the first member of the Markush grouping; conversely, noncyclic aliphatic alkenes result in an R group corresponding to the second member of the Markush group. The remaining halogen substituents may be fluorine, chlorine, bromine, iodine, or a combination thereof, but perfluoroalkenes are preferred. Examples of suitable compounds include hexafluorocyclobutene, tetrafluoroethylene, decafluorocyclohexene, 3,3,3-trichloro-1,1,2-trifluoropropene, and the like. The perhaloalkene is usually employed in a molar quantity approximately equal to or slightly in excess of that of the perfluorohexene-1,4-dione. Thus, an approximate cesium fluoride:perfluorohexane-1,4-dione:perhaloalkene molar ratio which is generally suitable is 2:1:1.

The reaction medium thus obtained is again permitted to attain an ambient temperature, and agitation is resumed until reaction equilibrium has been reached.

As the reaction proceeds to completion, a gradual decrease in the pressure within the reaction vessel can be observed; when the reaction is substantially complete, usually after from about 36 to about 60 hours, a relatively constant pressure will be evidenced within the vessel. Under reaction conditions as described above it is believed polymers are obtained, depending on promoter concentration and reaction time which contain an average number of repeating units in the range of about 4 to 8. On reducing the proportions of cesium fluoride promoter utilized and undertaking somewhat longer reaction times higher molecular weight polymers containing, predominantly, a number of repeating units up to 50 units is produced. With even less promoter and rather long reaction times employed, polymers with about 1000 or more repeating units are obtained. The polymer may be recovered by conventional methods of separation. Two such methods are illustrated in the examples which follow.

EXAMPLE VII

In a dry box having an anhydrous nitrogen atmosphere, 3.5 grams (0.023 mole) of anhydrous cesium fluoride and 10 milliliters of diethylene glycol dimethyl ether (diglyme) were charged to a glass reaction vessel, and 2.8 grams (0.0109 mole) of perfluorocyclohexane-1,4-dione were transferred into the reactor under a vacuum. The reaction medium was agitated for 16 hours using a conventional magnetic stirring bar and external motorized drive means, after which time a finely dispersed thick slurry had formed. Through a vacuum manifold, 2.0 grams (0.0123 mole) of hexafluorocyclobutene were added to the reaction medium which had been cooled to roughly −196° C. The reaction vessel was warmed to room temperature, and agitated for an additional 50 hours, after which time the volatile materials were removed under reduced pressure. It was subsequently learned that the only volatile material recovered in this step was unreacted hexafluorocyclobutene. The remaining contents of the reaction vessel were heated to 60° C. and subjected to a vacuum on the order of 1 micron Hg, whereupon the remaining liquid contents of the vessel were removed and collected in a −196° C. cold trap, leaving a solid residue of about 2.5 grams in the reaction vessel. When the contents of the trap were warmed to room temperature, two liquid layers were observed and were separated. The bottom layer weighing 0.7 gram was subsequently identified by NMR and infrared spectroscopy as having the following repeating unit:

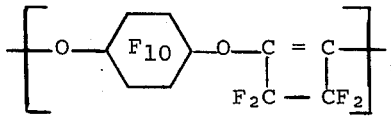

The spectroscopic analyses also indicated terminal perfluorocyclobutenyl moities. A small amount of the polymer was additionally recovered by diluting with water the upper layer, which was substantially comprised of diglyme, and following this with a solvent extraction step using methylene chloride.

EXAMPLE VIII

Using procedures similar to those described in the foregoing Example to charge the glass reaction vessel, 1.42 grams (0.00936 mole) of cesium fluoride, 5 milliliters of anhydrous diglyme, and 1.2 grams (0.00468 mole) of perfluorocyclohexane-1,4-dione were admixed for about 3 hours at room temperature to form a finely dispersed mixture. After connecting the reaction vessel to a vacuum line and cooling it with liquid nitrogen, 0.77 gram (0.00468 mole) of hexafluorocyclobutene was added thereto. The reaction mixture was then agitated at an ambient temperature for 41 hours. Volatile components were removed on a vacuum line, and thereafter the reactor was opened and 20 milliliters of Freon 113 brand of trichlorotrifluoroethane were added thereto. The resulting mixture was agitated and filtered to remove solid by-products. After the solvent was removed, 0.4 g. of a viscous, amber colored liquid remained. This liquid was washed twice with water and distilled under a high vacuum to yield a viscous, clear, colorless oil which was subsequently identified by NMR and infrared spectroscopy to contain the following as a repeating unit

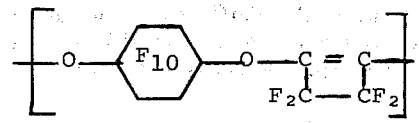

Figure 3:
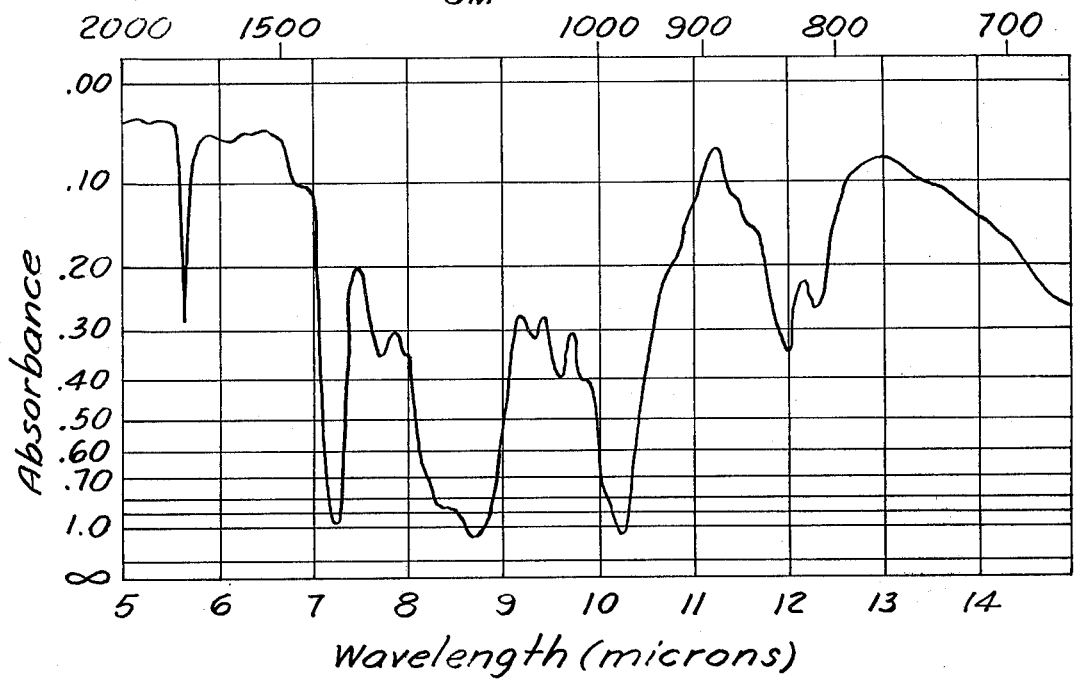
FIG. 3 is another reproduced recording showing the absorption of light in the infrared region of the spectrum by the polymer prepared as described in Examples VII and VIII.

The polymers prepared as described in Examples VII and VIII had a boiling point of 50° C. at a pressure of 1 μHg. The infrared spectra is shown in FIG. 3. Characteristic peaks were observed in the fluorine resonance spectrum (56.4 MHz) at 108, 113, 117, 120, 121 to 133 (multiplet), 139, and 140, expressed as δ units relative to CFCl$_3$.

On repeating substantially the processes described in Examples VII and VIII but using, respectively, octafluorobut-1-ene, tetrafluoroethylene, decafluorocyclohexene, or 3,3,3-trichloro-1,1,2-trifluoropropene, or perfluoroheptene-1 in place of hexafluorocyclobutene, polymers having the following repeating units are obtained, respectively, in similar amount:

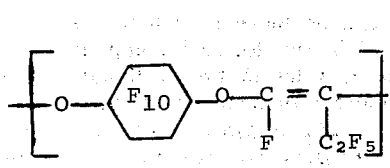

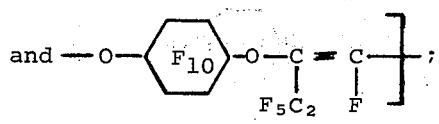

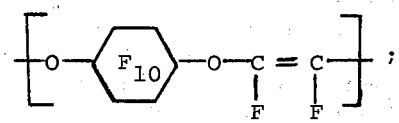

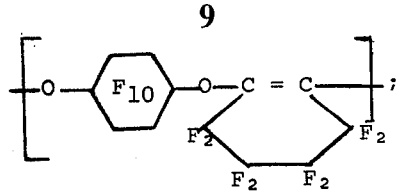

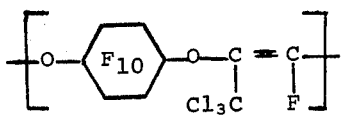

and 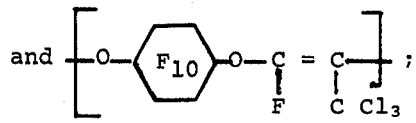

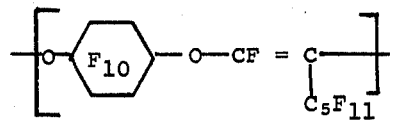

and 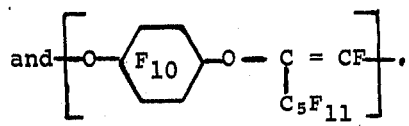

C. Preparation of
Octafluoro-1,1,4,4-cyclohexanetetraol

The above named stable dihydrate of perfluorocyclohexane-1,4-dione is recovered from the reaction medium obtained in the hereinbefore described polymer preparation by treating the completed reaction medium with a solubilizing amount of water and recovering the compound from the water using conventional solvent extraction techniques.

One specific approach which may be taken in practicing the above-described method is to admix the entire completed reaction medium with water. Two layers are formed, the heavier oil layer comprising the polymer and the lighter aqueous layer comprising an aqueous solution of octafluoro-1,1,4,4-cyclohexanetetraol and cesium fluoride. Extraction of the aqueous layer with any common substantially water immiscible solvent such as ethyl ether, methylene chloride, carbon tetrachloride and the like, followed by evaporation of the solvent, yields a white crystalline solid which has been identified as octafluoro-1,1,4,4-cyclohexanetetraol.

Alternatively, the dihydrate compound may be recovered from the reaction mixture by treating only the solid components of said mixture with water and recovering the dissolved compound from the aqueous solution using conventional solvent extraction techniques as hereinbefore described. A specific instance in which this latter approach was used is described in the following example.

EXAMPLE IX

Figure 4:
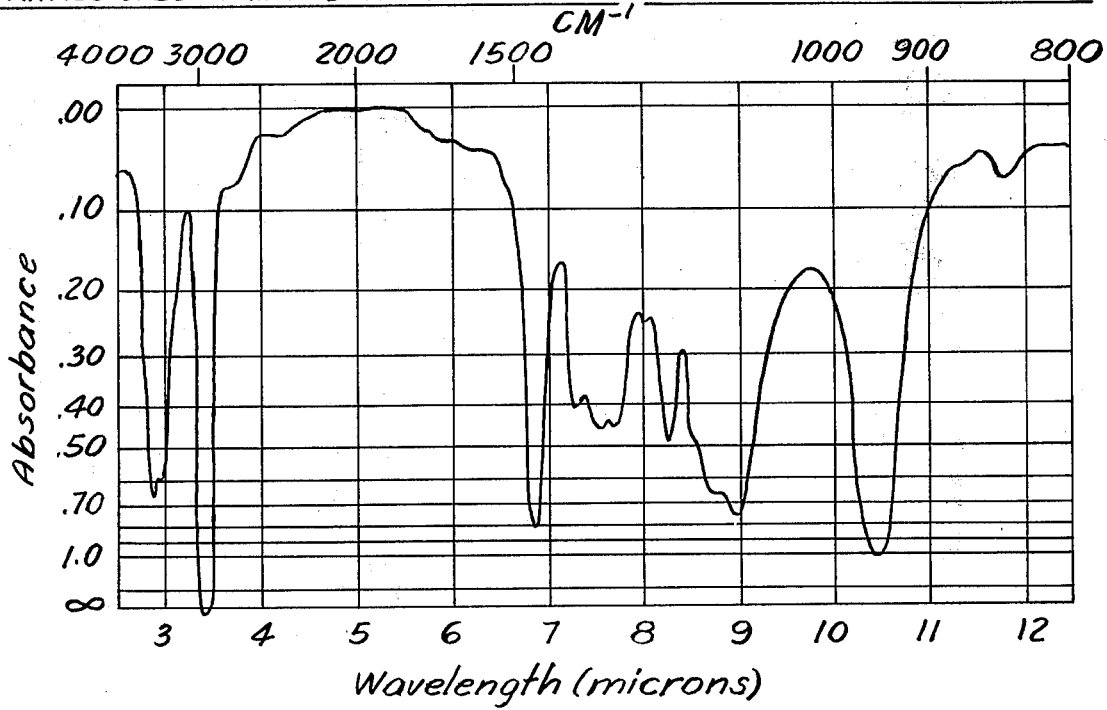
FIG. 4 is still another reproduced recording showing the absorption of light in the infrared region of the spectrum by the compound prepared as described in Example IX and identified as octafluoro-1,1,4,4-cyclohexanetetraol.

Reference is made to Example VII wherein removal of the liquid products of the reaction by heating under a partial vacuum was described, said step leaving a solid residue of about 2.5 grams. This residue was treated with 200 milliliters of water, and the resulting aqueous solution extracted with four 25 milliliter aliquots of ethyl ether. The ethyl ether was removed by evaporation, leaving 1.5 grams of a white crystalline solid. The solid was purified readily by sublimation at about 110° C. and a pressure of 15 mm Hg. The compound melted at 175°–176° C. in a closed capillary, and was identified as octafluoro-1,1,4,4-cyclohexanetetraol, having a molecular weight of 292.08 grams per mole. The infrared spectrum of this compound made in Nujol mull is shown in FIG. 4.

What is claimed is:
1. Perfluorocyclohexene-1,4-dione.
2. A compound useful in the synthesis of thermally stable elastomeric polymers, said compound being characterized by the following properties:
   a. boiling point of about 140° C. at atmospheric pressure;
   b. molecular weight of 218.056 grams per mole;
   c. characteristic absorption in the infrared region of the spectrum substantially corresponding to that shown in FIG. 2;
   d. a fluorine resonance spectrum at 56.4 MHz with principal characteristic absorption peaks at 131.0 and 126.1, expressed in δ units relative to $CFCl_3$; and
   e. a mass spectrum having an $M^+$ peak at 218 m/e units, and further characteristic peaks at 168, and 109 m/e units.

* * * * *

UNITED STATES PATENT AND TRADEMARK OFFICE
CERTIFICATE OF CORRECTION

PATENT NO. : 3,931,325
DATED : January 6, 1976
INVENTOR(S) : Harold E. Doorenbos and Hughie R. Frick It is certified that error appears in the above-identified patent and that said Letters Patent are hereby corrected as shown below:

On the cover page, under "OTHER PUBLICATIONS", on line 2, change "95" to --75--.

In column 6, line 29, delete "uusual" and insert --usual--.

In column 6, line 63, delete "fluorohexene" and insert --fluorohexane--.

In column 7, line 58, change "moities" to --moieties--.

In column 8, line 35, delete "or".

Signed and Sealed this first Day of June 1976

[SEAL]

Attest:

RUTH C. MASON
Attesting Officer

C. MARSHALL DANN
Commissioner of Patents and Trademarks